US010870894B2

(12) United States Patent
O'Hara et al.

(10) Patent No.: US 10,870,894 B2
(45) Date of Patent: *Dec. 22, 2020

(54) METHODS FOR MEASURING ENZYME ACTIVITY USEFUL IN DETERMINING CELL VIABILITY IN NON-PURIFIED SAMPLES

(71) Applicant: Momentum Bioscience, LTD., Cardiff (GB)

(72) Inventors: Shawn Mark O'Hara, Richboro, PA (US); Daniel Zweitzig, Feasterville, PA (US)

(73) Assignee: MOMENTUM BIOSCIENCE, LTD.

( * ) Notice: Subject to any disclaimer, the term of this patent is extended or adjusted under 35 U.S.C. 154(b) by 113 days.

This patent is subject to a terminal disclaimer.

(21) Appl. No.: 14/737,736

(22) Filed: Jun. 12, 2015

(65) Prior Publication Data

US 2018/0230551 A1    Aug. 16, 2018

Related U.S. Application Data

(62) Division of application No. 13/641,480, filed as application No. PCT/US2011/032600 on Apr. 15, 2011, now abandoned.

(60) Provisional application No. 61/325,413, filed on Apr. 19, 2010, provisional application No. 61/324,949, filed on Apr. 16, 2010, provisional application No. 61/324,939, filed on Apr. 16, 2010.

(51) Int. Cl.

| *C12Q 1/6888* | (2018.01) |
|---|---|
| *C12Q 1/04* | (2006.01) |
| *C12Q 1/25* | (2006.01) |
| *C12Q 1/42* | (2006.01) |
| *C12Q 1/48* | (2006.01) |

(52) U.S. Cl.
CPC ............ *C12Q 1/6888* (2013.01); *C12Q 1/04* (2013.01); *C12Q 1/25* (2013.01); *C12Q 1/42* (2013.01); *C12Q 1/48* (2013.01)

(58) Field of Classification Search
None
See application file for complete search history.

(56) References Cited

U.S. PATENT DOCUMENTS

| 5,413,906 A * | 5/1995 | Eberle ................ C12Q 1/48 435/15 |
|---|---|---|
| 5,629,154 A | 5/1997 | Kim |
| 5,635,350 A | 6/1997 | Eberle et al. |
| 5,695,932 A | 12/1997 | West |
| 5,807,669 A | 9/1998 | Schupbach et al. |
| 5,863,726 A | 1/1999 | Harley |
| 5,891,639 A | 4/1999 | Harley |
| 6,054,278 A | 4/2000 | Dodge et al. |
| 2009/0275063 A1 | 11/2009 | Green et al. |
| 2013/0196318 A1 | 8/2013 | O'Hara et al. |

FOREIGN PATENT DOCUMENTS

| EP | 0385410 A2 | 9/1990 |
|---|---|---|
| EP | 1205559 | 6/2009 |
| EP | 2558600 B1 | 10/2017 |
| JP | 501953 | 4/1992 |
| JP | 505942 | 9/1993 |
| JP | 1994509477 | 3/1996 |
| WO | 9006320 | 6/1990 |
| WO | 9006373 A1 | 6/1990 |
| WO | 9204467 A1 | 3/1992 |
| WO | 2001027318 A2 | 4/2001 |
| WO | 2004015141 | 2/2004 |
| WO | 2004015141 A2 | 2/2004 |
| WO | 2009007719 | 1/2009 |
| WO | 2009007719 A2 | 1/2009 |
| WO | 2011130584 A2 | 10/2011 |

OTHER PUBLICATIONS

Hyone-Myong Eun. Enzymology Primer for Recombinant DNA Technology. 1996, pp. 491-565.*
Garcia-Diaz et al. CRC Crit Rev Plant Sci. Mar. 2007; 26(2):105-122.*
Coffin JM et al. Editors. Cold Spring Harbor (NY): Cold Spring Harbor Laboratory Press; 1997 retrieved on Jun. 21, 2018 from https://www.ncbi.nlm.nih.gov/books/NBK19424/.*
Silver et al. Nucleic Acids Research, 1993 vol. 21, No. 15 3593-3594 1993.*
Jarvinen et al. BMC Microbiology, 9:161 pp. 1-16 Aug. 10, 2009.*
Korean Office Action for 10-2012-7030167 dated Oct. 30, 2017.
European Search Report for EP 17194583.5 dated Nov. 29, 2017.
Liu, Huanting, et al., "An efficient one-step site-directed deletion, insertion, single and multiple-site plasmid mutagenesis protocol", BMC Biotechnology, Biomed Central LTD., London, GB, vol. 8, No. 1, Dec. 2008, p. 91.
Australian Examination Report for AU 2016203878 dated Oct. 19, 2017.
Sharon Banin et al, "The LiMA Technology: Measurement of ATP on a Nucleic Acid Testing Platform", Clinical Chemistry, (Sep. 21, 2007), vol. 53, No. 11, doi:10.1373/clinchem.2007.091140, ISSN 0009-9147, pp. 2034-2036, XP055106846 DOI: http://dx.doi.org/10.1373/clinchem.2007.091140.
Yu Liming et al, "Fluorescence-based, high-throughput DNA polymerase assay.", Biotechniques Oct. 2002, (Oct. 2002), vol. 33, No. 4, ISSN 0736-6205, pp. 938-941, XP001526275.

(Continued)

*Primary Examiner* — Oluwatosin A Ogunbiyi
(74) *Attorney, Agent, or Firm* — Quarles & Brady LLP

(57) ABSTRACT

Methods for detecting microorganisms, in particular detection of bacteria and methods for measuring enzyme activity, such as Deoxyribonucleic acid (DNA) polymerase activity are disclosed. The aforesaid methods include, but are not limited to such methods performed on microbial crude lysates, useful for determining microbial enzyme activities, which can be linked to amplification signal generators such as real-time Polymerase Chain Reaction (PCR) techniques, thereby enabling determination of microbial pathogens in samples such as unpurified blood and other body fluids. Moreover, the disclosed embodiments also relate to reagents for use in such methods, and to test kits comprising such reagents for carrying out the methods.

14 Claims, 9 Drawing Sheets

(56) References Cited

OTHER PUBLICATIONS

Ma C et al, "Real-time monitoring of DNA polymerase activity using molecular beacon", Analytical Biochemistry, Academic Press Inc, New York, vol. 353, No. 1, doi:10.1016/J.AB.2006.02.006, ISSN 0003-2697, (Jun. 1, 2006), pp. 141-143, (Jun. 1, 2006), XP024942209 DOI: http://dx.doi.org/10.1016/j.ab.2006.02.006.
Nolan et al. (2006) "Quantification of mRNA using real-time RT-PCR" Nat Protoc. 1(3):1559-82 DOI: 10.1038/nprot.2006.236.
Seville M et al, "Fluorometric Assay for DNA Polymerases and Reverse Transciptase", Biotechniques, Informa Healthcare, US, (Oct. 1, 1996), vol. 21, No. 4, ISSN 0736-6205, pp. 664-672, XP001204838.
Tveit, Heidi and Kristensen, Tom (2001) "Fluorescence-Based DNA Polymerase Assay" Analytical Biochemistry, vol. 289, Issue 1, pp. 96-98.
D. R. Zweitzig et al, "Characterization of a novel DNA polymerase activity assay enabling sensitive, quantitative and universal detection of viable microbes", Nucleic Acids Research, (Apr. 11, 2012), vol. 40, No. 14, doi:10.1093/nar/gks316, ISSN 0305-1048, pp. e109-e109, XP055106744 DOI: http://dx.doi.org/10.1093/nar/gks316.
Arnold BA, Hepler RW, Keller PM. One-step fluorescent probe product-enhanced reverse transcriptase assay. Biotechniques. Jul. 1998; 25(1): 98-106.
Brorson K, Xu Y, Swann PG, Hamilton E, Mustafa M, de Wit C, Norling LA, Stein KE. Evaluation of a quantitative product-enhanced reverse transcriptase assay to monitor retrovirus in mAb cell-culture. Biologicals. Mar. 2002; 30(1): 15-26.
Cano MIN, Dungan JM, Agabian N, Blackburn EH. Telomerase in kinetoplastid parasitic protozoa. Proceedings of the National Academy of Sciences of the United States of America. 1999; 96(7): 3616-3621.
Gauthier LR, Granotier C, Soria JC, Faivre S, Boige V, Raymond E, Boussin FD.: Detection of circulating carcinoma cells by telomerase activity. Br J Cancer. Mar. 2, 2001; 84(5): 631-5.
Howard C.R. (1978) Journal of medical virology 3:81-86.
Kim NW, Piatyszek MA, Prowse KR, Harley CB, West MD, Ho PL, Coviello GM, Wright WE, Weinrich SL and Shay JW. Specific association of human telomerase activity with immortal cells and cancer. Science. 1994; 266: 2011-2015.
Lim, Daniel V. (2001). eLS. John Wiley. doi: 10.1038/npg.els.0000459. ISBN 9780470015902.
Lin JJ, Zakian VA. An in vitro assay for Saccharomyces telomerase requires EST1. Cell. Jun. 30, 1995; 81(7): 1127-35.
Losick R, Watson JD, Baker TA, Bell S, Gann A, Levine MW (2008). Molecular biology of the gene (6th ed.). San Francisco: Pearson/Benjamin Cummings. ISBN 0-8053-9592-X.
Lugert R, König H, Kurth R, Tönjes RR. Specific suppression of false-positive signals in the product-enhanced reverse transcriptase assay. Biotechniques. Feb. 1996; 20(2)210-217.
Maudru T., Peden K. Elimination of background signals in a modified polymerase chain reaction-based reverse transcriptase assay. Journal of Virological Methods, 1997, 66 (2), pp. 247-261.
Nugent CI, Lundblad V. The telomerase reverse transcriptase: components and regulation. Genes & Development. 1998; 12: 1073-1085.
Pyra H, Böni J, Schupbach J. Ultrasensitive retrovirus detection by a reverse transcriptase assay based on product enhancement. Proceedings of the National Academy of Sciences of the United States of America. 1994; 91(4): 1544-1548.
Raj DK, Das BR, Dash AP, Supakar PC. Identification of telomerase activity in gametocytes of Plasmodium falciparum. Biochemical and Biophysical Research Communications. 2003; 309 (3): 685-8.
Rubiano CC, Wasserman M. Detection of telomerase activity in Plasmodium falciparum using a nonradioactive method. Memórias do Instituto Oswaldo Cruz 2003, 98(5), 693-695.
Tzertzinis G, Tabor S, Nichols NM., RNA-dependent DNA polymerases. Curr Protoc Mol Biol. Oct. 2008; Chapter 3: Unit 3.7.

Vellore J, Moretz SE, Lampson BC. A group II intron-type open reading frame from the thermophile Bacillus (Geobacillus) stearothermophilus encodes a heat-stable reverse transcriptase. Appl Environ Microbiol. Dec. 2004; 70 (12): 7140-7.
Canadian Office Action for 2,796,676 dated Feb. 6, 2017.
Eurasian Office Action for 201291001/28 dated Aug. 29, 2016.
Israeli Office Action dated Nov. 12, 2017.
Japanese Office Action for 2013-505162 dated Jan. 24, 2017.
Korean Office Action for 10-2012-7030167 dated Jan. 18, 2017.
Crow, et al. Momentum Bioscience Poster, 2014.
Schwartz, et al PNAS (2009), 106:48 pp. 20294-20299.
Alberts B; Johnson A; Lewis J; et al. Molecular Biology of the Cell (4th ed.). Garland Science. 2002, p. 1424 and p. 1437.
ANON. Enzyme Resource Guide: Polymerases. Promega Corporation. 1998, 30 pages.
Becker Y. Replication of Viral and Cellular Genomes. Martinus Nijhoff Publishing. 1983, p. 278.
Dutton G. Speedy Sepsis Dx via Molecular Markers. GEN. 2016; 36(21):8-9.
Ecker DJ, Sampath R, Li H, Massire C, Matthews HE, Toleno D, Hall TA, Blyn LB, Eshoo MW, Ranken R, Hofstadler SA, Tang YW. New technology for rapid molecular diagnosis of bloodstream infections. Expert Rev Mol Diagn. 2010;10(4):399-415.
Eun HM. Enzymology Primer for Recombinant DNA Technology, Chapter 6—DNA Polymerases. Academic Press. 1996, p. 345.
European Patent Office Communication for application EP11769633.6, including Letter from Opponent, dated Mar. 11, 2019, 44 pages.
European Patent Office Communication for application EP11769633.6, dated Jun. 11, 2019, 1 page.
Fajkus J. Detection of telomerase activity by the TRAP assay and its variants and alternatives. Clin Chim Acta. 2006;371(1-2):25-31.
Griffiths AJF, Gelbart WM, Lewontin RC, Miller JH, et al. Modern Genetic Analysis (2nd ed.). W. H. Freeman. 2002, p. 26,661 and 675.
Hubscher U, Spadari S, Villani G, Maga G. DNA Polymerases—Discovery, Characterization and Functions in Cellular DNA Transactions. World Scientific Publishing. 2010, p. 61 and 64-68.
Johnson LM, Snyder M, Chang LM, Davis RW, Campbell JL. Isolation of the gene encoding yeast DNA polymerase I. Cell. 1985;43(1):369-77.
Korea Intellectual Property Office Action, for application KR10-2018-7021294, dated May 28, 2019, English Translation, 8 pages.
Lovatt A, Black J, Galbraith D, Doherty I, Moran MW, Shepherd AJ, Griffen A, Bailey A, Wilson N, Smith KT. High throughput detection of retrovirus-associated reverse transcriptase using an improved fluorescent product enhanced reverse transcriptase assay and its comparison to conventional detection methods. J Viral Methods. 1999;82(2):185-200.
Oussalah A, Ferrand J, Filhine-Tresarrieu P, Aissa N, Aimone-Gastin I, Namour F, Garcia M, Lozniewski A, Gueant JL. Diagnostic Accuracy of Procalcitonin for Predicting Blood Culture Results in Patients With Suspected Bloodstream Infection. Medicine. 2015;94(44):e1774.
Spellberg B, Guidos R, Gilbert D, Bradley J, Boucher HW, Scheid WM, Bartlett JG, Edwards J Jr. The epidemic of antibiotic-resistant infections: a call to action for the medical community from the Infectious Diseases Society of America. Clin Infect Dis. 2008;15;46(2):155-64.
European Patent Office Summons to Attend Oral Proceedings for application EP11769633.6, dated Mar. 14, 2019, 12 pages.
Japanese Office Action for JP 2017-086485 dated Apr. 17, 2018.
Tveit, Heidi, et al., "Fluorescence-Based DNA Polymerase Assay", Analytical Biochemistry, 2001, vol. 289, No. 1, pp. 96-98.
Zweitzig, Daniel, et al., "Characterization of a novel DNA polymerase activity assay enabling sensitive, quantitative and universal detection of viable microbes", Nucleic Acids Research, 2012, vol. 40, No. 14, pp. e109(1-12).
Dawn M. Simon and Steven Zimmerly, A diversity of uncharacterized reverse transcriptases in bacteria, Nucleic Acids Research, Nov. 12, 2008, pp. 7219-7229, vol. 36, No. 22, Department of Biological Sciences, University of Calgary, Calgary, Alberta, Canada.

\* cited by examiner

METHODS FOR MEASURING ENZYME ACTIVITY USEFUL IN DETERMINING CELL VIABILITY IN NON-PURIFIED SAMPLES

CROSS REFERENCE TO RELATED APPLICATIONS

This application is a divisional application of U.S. application Ser. No. 13/641,480, now abandoned, which is the U.S. National Stage of International Application PCT/US2011/032600, filed on Apr. 15, 2011, which claims the benefit of priority to U.S. Provisional Application No. 61/325,413, filed on Apr. 19, 2010, to U.S. Provisional Application No. 61/324,949, filed on Apr. 16, 2010, and to U.S. Provisional Application No. 61/324,939, filed on Apr. 16, 2010, which applications are incorporated herein by reference as if set forth in their entireties.

FIELD OF THE INVENTION

The present invention relates generally to the field of detecting microorganisms, and more particularly to the detection of bacteria. Also provided by the invention are improved methods of detecting microorganisms that are highly sensitive, are applicable to non-purified samples, and have numerous applications, together with assay kits, which rely upon the presence of ligase and/or phosphatase as an indicator of bacterial viability.

BACKGROUND OF THE INVENTION

Measuring the presence and levels of certain molecules which are associated with cell viability is important in a number of contexts. For example, measuring levels of ATP is useful in mammalian cells for growth analysis and toxicology purposes.

Culture approaches can be used to detect small numbers of bacteria but such techniques require several days to complete, especially when attempting to detect small numbers of bacteria and also when detecting slower growing microorganisms.

Alternatively, tests may be carried out based upon measuring the presence of a molecule which can be linked to the presence in the sample of a contaminant cell or organism. The most commonly detected molecule is Adenosine Triphosphate (ATP). Detection of DNA and RNA has also been proposed, although the correlation between the presence of DNA and RNA and viability is not clear-cut due to the variable persistence of nucleic acids in cells post death (Keer & Birch, Journal of Microbiological Methods 53 (2003) 175-183). Detection of adenylate kinase as an indicator of viability has also been proposed (Squirrell D J, Murphy M J, Leslie R L, Green J C D: A comparison of ATP and adenylate kinase as bacterial cell markers: correlation with agar plate counts, in Bioluminescence and Chemiluminescence Progress and Current Applications. Edited by: Stanley R A, Kricka L J. John Wiley and Sons; 2002 and WO 96/02665). A routinely employed method for determining ATP levels involves the use of bioluminescence. The method uses the ATP dependency of the reaction in which light emitting luciferase catalyzes oxidation of luciferin. The method may be used to measure relatively low concentrations of ATP. Kits useful for detecting ATP using bioluminescence are commercially available from Roche, New Horizons Diagnostics Corp, Celsis etc. However, a number of problems exist with respect to bioluminescence detection. For example, detection of microbial ATP only, in the presence of ATP from non-microbial sources can be a problem. This problem has been solved to a certain degree by use of filters which can separate bacteria from nonbacterial sources of ATP, thus providing a more accurate signal.

Accordingly, it can be seen that a number of problems exist with respect to the conventional art of microbe detection. In order to further address such problems, detection of ligases has been proposed, such as described in published patent application WO/1996/002665, published Feb. 1, 1996, there is disclosed a method for determining the presence and/or amount of microorganisms and/or their intracellular material present in a sample characterized in that the amount of adenylate kinase in the sample is estimated by mixing it with adenosine diphosphate (ADP), determining the amount of adenosine triphosphate (ATP) produced by the sample from this ADP, and relating the amount of ATP so produced to the presence/or amount of adenylate kinase and to microorganisms and/or their intracellular material, wherein the conversion of ADP to ATP is carried out in the presence of magnesium ions at a molar concentration sufficient to allow maximal conversion of ADP to ATP. The amount of magnesium present is preferably such that there is sufficient to provide one mole of magnesium for one mole of ADP such that all of the ADP molecules may be associated with at least one magnesium ion.

In published patent application WO/2009/007719, published Jan. 15, 2009, entitled DETECTION OF MICROORGANISMS BASED ON THEIR NAD-DEPENDENT DNA LIGASE ACTIVITY ligases, in particular NAD-dependent ligases, are disclosed as a useful indicator of the presence of a (viable) microorganism in a sample. Ligases are enzymes which catalyze ligation of nucleic acid molecules. The ligation reaction requires either ATP or NAD+ as co-factor depending upon the ligase concerned. In this disclosure, the use of NAD-dependent ligase activity is utilized as an indicator of the presence of a (viable) microorganism in a sample. The link between NAD-dependent ligase activity and viability is central to the invention disclosed in this application, (Korycka-Machala et al., Antimicrobial Agents and Chemotherapy, August 2007, p 2888-2897), since it allows the activity of this enzyme to be used as an indicator of viable microbial cells, in particular of bacterial origin, in the sample. However, in the experiments leading to the development of the present invention, it was found that the techniques and teachings described in this published patent application WO/2009/007719 could not be applied to the determination of viable microorganisms in unpurified samples, such as crude microbial lysates, blood or blood cultures, thereby constituting a major drawback of the technology as described in this reference. However, it has been discovered that these methodologies, too, have problems. For example, it has been found that in general the conventional ligase substrate assay design and resultant detection signal thereof, as disclosed in the above-reference patent application, is not ligase specific when applied to its intended sample type (blood derived microbe crude cell lysates). It is these problems which the present invention seeks to address and to overcome.

SUMMARY OF THE INVENTION

In contrast to the conventional methods described above, in one aspect the present invention is directed to the detection of enzymes such as polymerases, in preferred embodiments DNA or RNA polymerases, as a useful indicator of the presence of a (viable) microorganism or microbe in a sample, in particular a sample that is, for example, a crude microbial lysate or unpurified blood or blood culture. The association discovered in accordance with the present invention between enzyme, e.g., polymerase, activity and viability of microorganisms or microbes enables the detection of activity of these enzymes to be used as an indicator of viable microbial cells, in particular of bacterial origin, in the sample.

Similarly, the invention provides, in a preferred embodiment, methods for detecting a DNA or RNA polymerase as an indicator of the presence of a microorganism in a sample. Such a method can comprise:

(a) contacting the sample with a nucleic acid molecule which acts as a substrate for polymerase activity in the sample, (b) incubating the thus contacted sample under conditions suitable for polymerase activity; and (c) determining the presence (and/or the amount) of a nucleic acid molecule resulting from the action of the microorganism polymerase on the substrate nucleic acid molecule to indicate the presence of the microorganism.

In addition, the present invention provides reagents useful in the foregoing described methods, and assay kits comprising such reagents useful for performing the methods.

In another aspect, the present invention provides improvements to the methods, compositions and kits described in published patent application WO/2009/007719, published Jan. 15, 2009, entitled DETECTION OF MICRO-ORGANISMS BASED ON THEIR NAD-DEPENDENT DNA LIGASE ACTIVITY, which published application identifies ligases, in particular NAD-dependent ligases, as a useful indicator of the presence of a (viable) microorganism or microbe.

The entire disclosure contained in said WO/2009/007719 is hereby incorporated by reference and made a part of this application.

The present invention accordingly provides improvements to the methods, and compositions and kits based thereon as disclosed in WO/2009/007719, of detecting an enzyme selected from the group consisting of NAD-dependent ligase, or a phosphatase, or a mixture of the foregoing, as an indicator of the presence of a microorganism in a sample, which improved methods comprise:

(a) contacting the sample with a nucleic acid molecule which acts as a substrate for enzyme activity in the sample, while not allowing interfering signals from DNA polymerase, (b) incubating the thus contacted sample under conditions suitable for enzyme activity; and (c) determining the presence (and/or the amount) of an enzyme modified nucleic acid molecule resulting from the action of the selected enzyme or mixture on the substrate nucleic acid molecule to indicate the presence of the microorganism.

Thus, it will be appreciated that the improved methods of the invention are useful for identifying all microorganisms in which such enzymes or mixtures thereof are (or have been) expressed.

As stated herein, the first step in the method comprises contacting the sample with a nucleic acid molecule which acts as a substrate for enzyme activity in the sample, while not allowing interfering signals from DNA polymerase. It is thus to be appreciated that any suitable ligatable molecule which can be specifically detected once ligated may be utilized in the methods of the invention.

DETAILED DESCRIPTION OF THE INVENTION

Figure 1A:
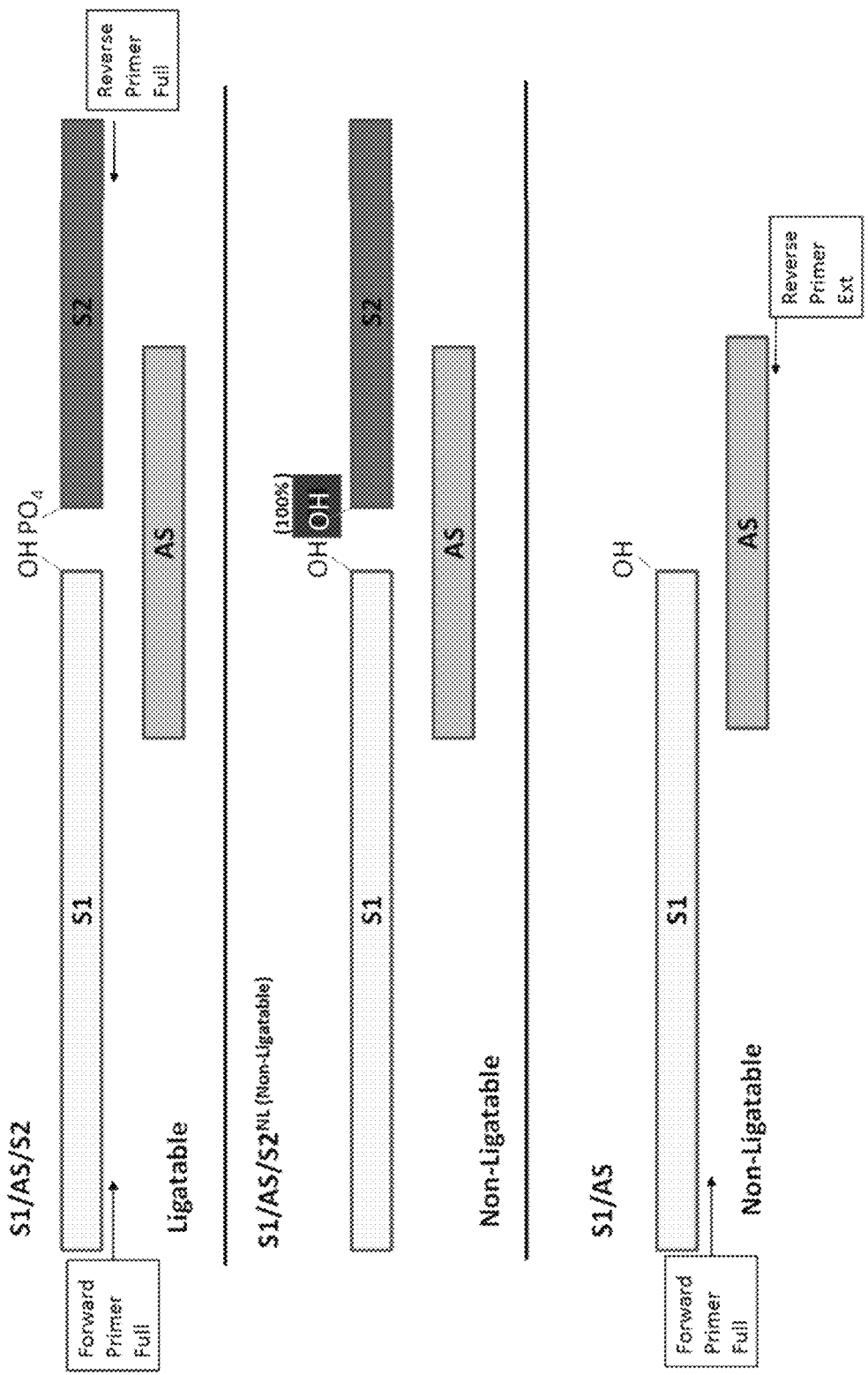
FIG. 1A. Template diagrams used in experiments conducted in accordance with the present invention as described herein.
Figure 1B:
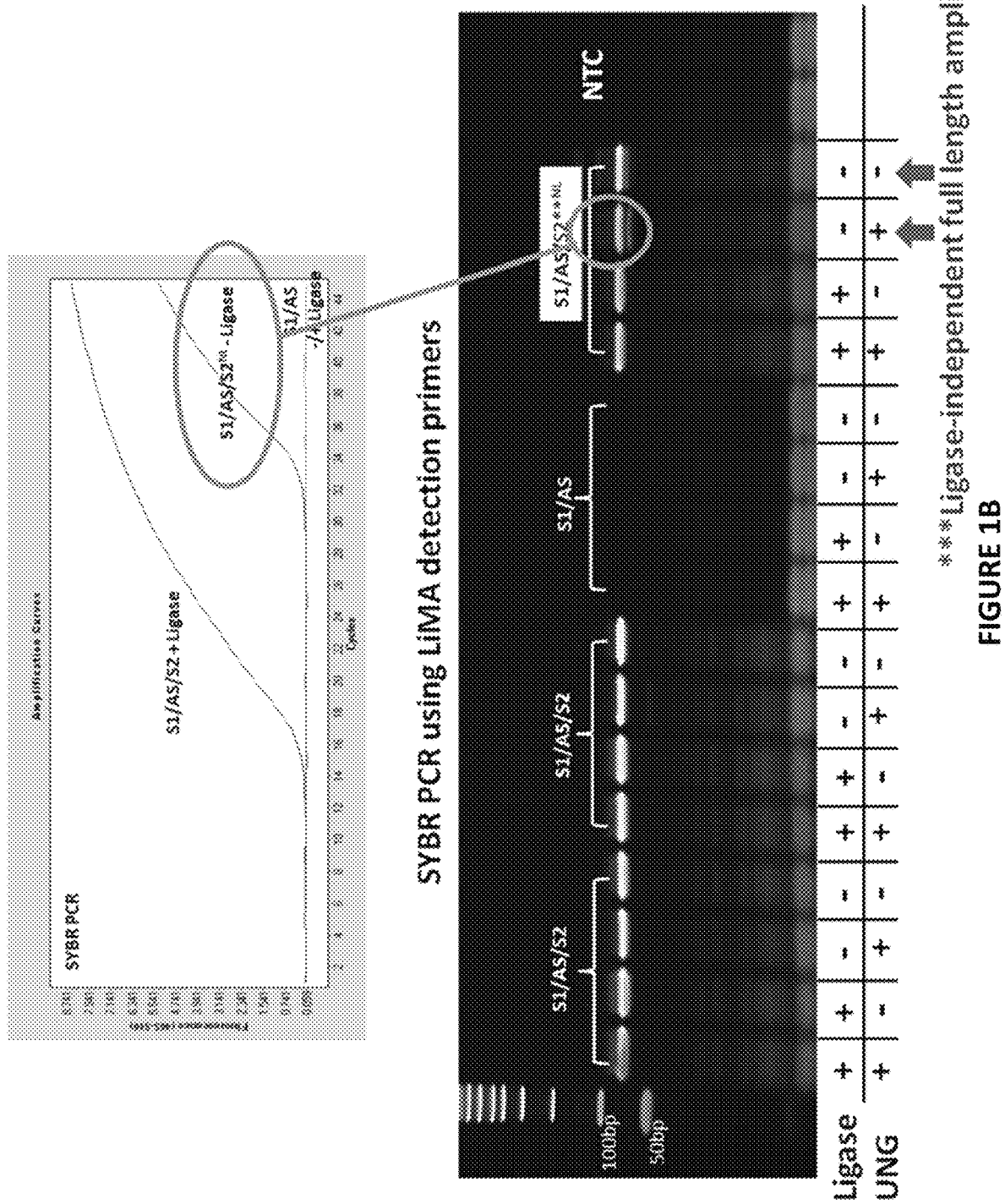
FIG. 1B. Graphical representations of results produced in experiments conducted in accordance with the present invention as described herein.
Figure 1C:
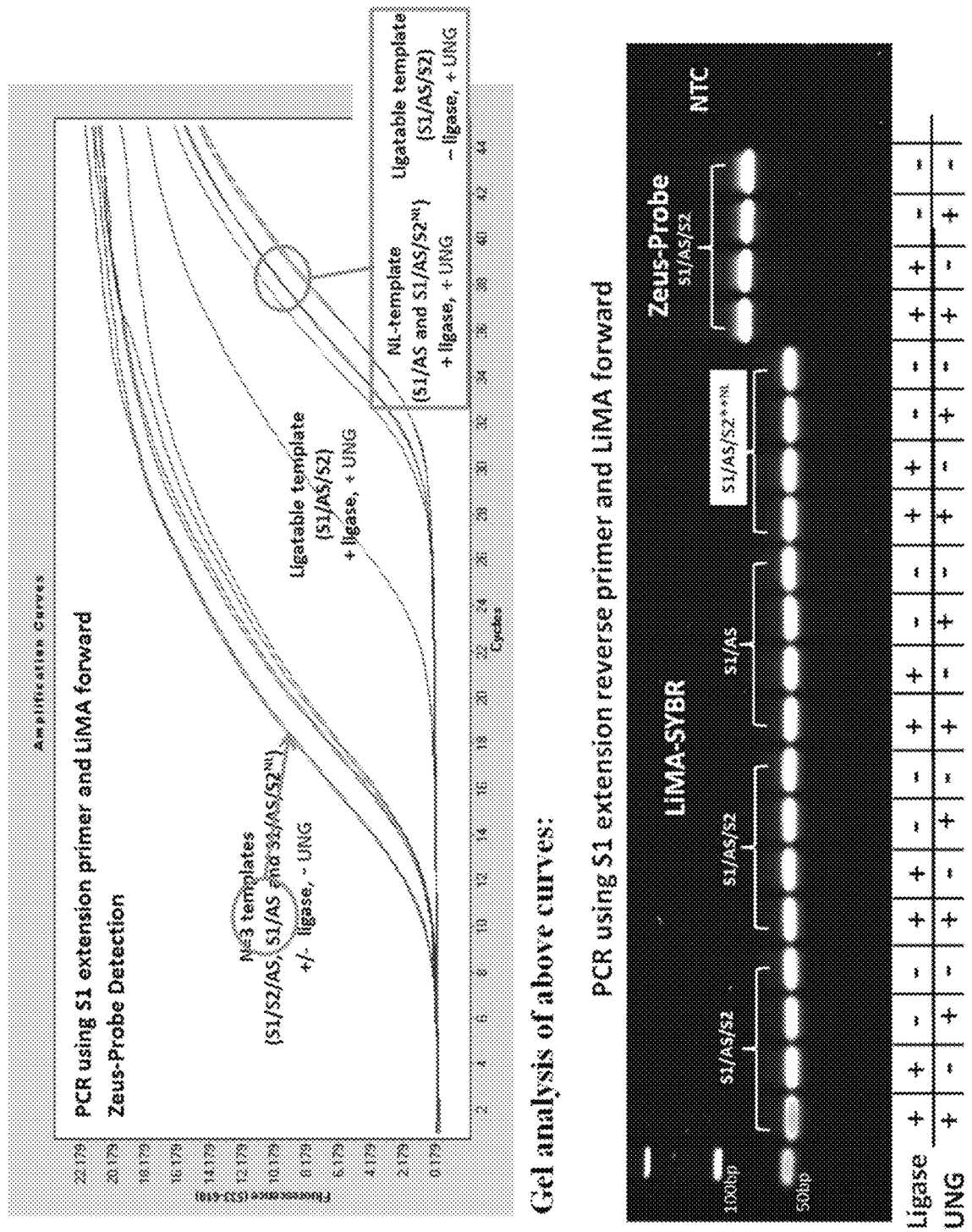
FIG. 1C. Graphical representations of results produced in experiments conducted in accordance with the present invention as described herein.
Figure 1D:
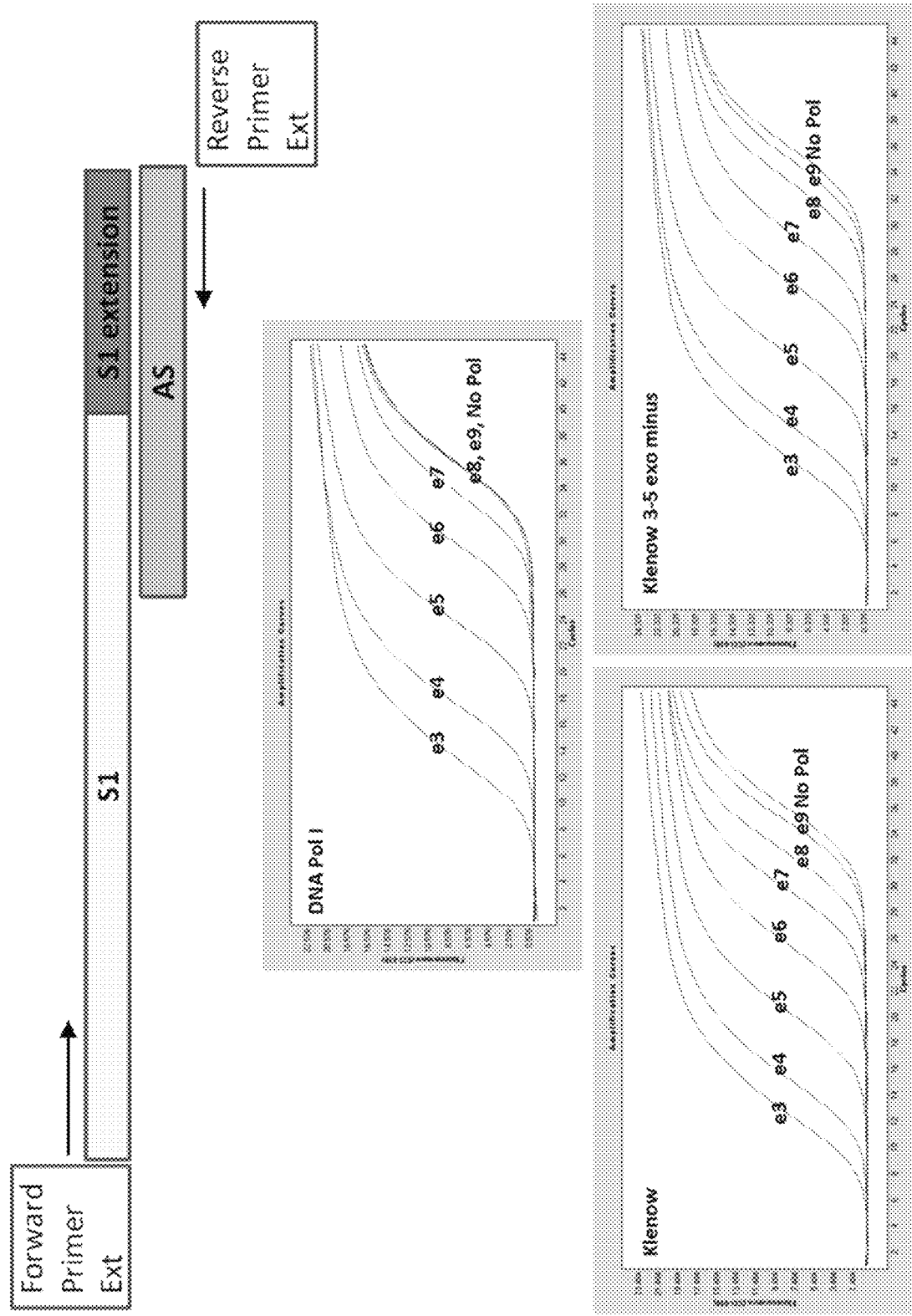
FIG. 1D. Template diagrams used in and graphical representations of results produced by experiments conducted in accordance with the present invention as described herein.
Figure 2A:
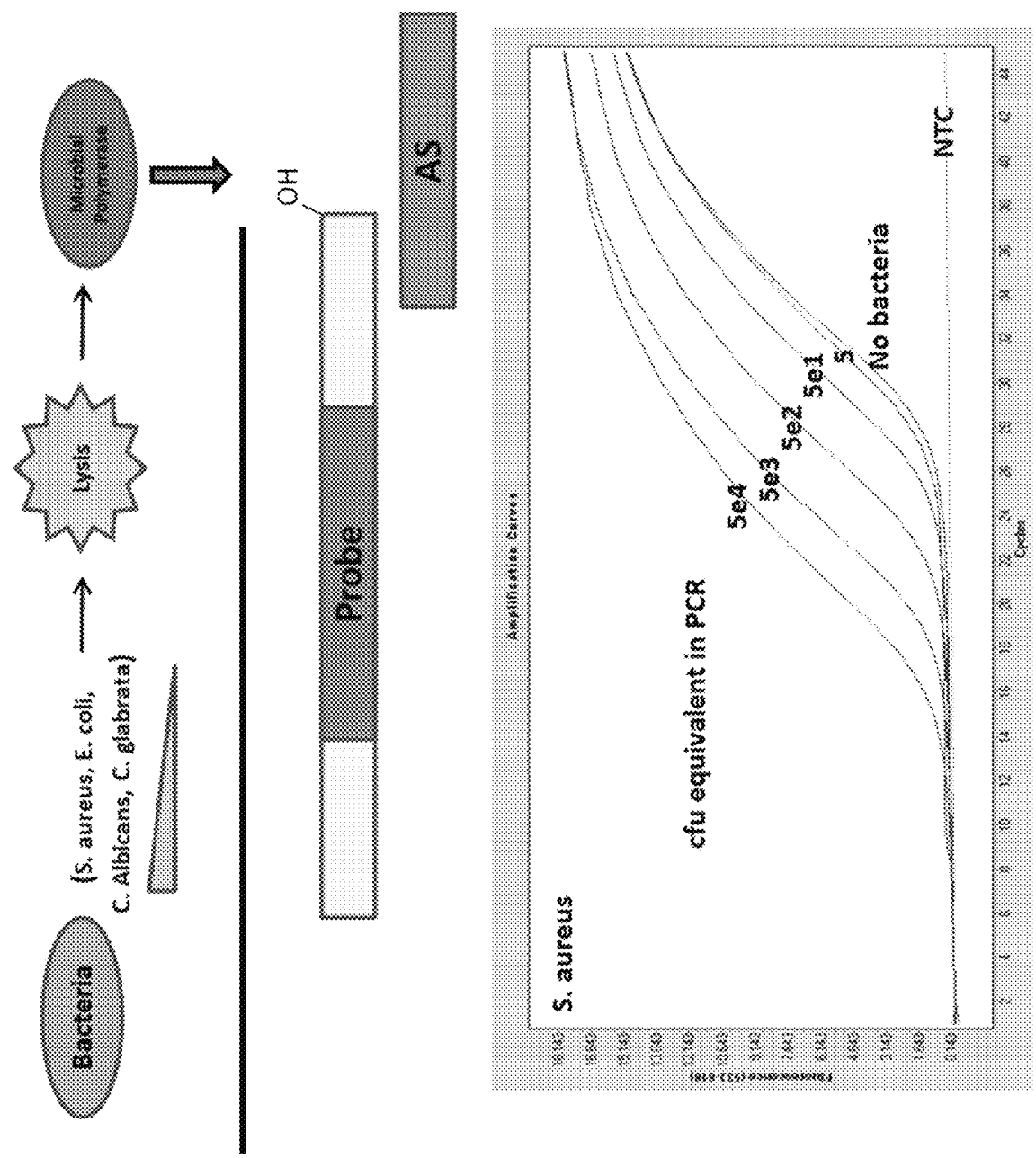
FIG. 2A. Graphical representations showing that Non-Ligate-able, Polymerase favorable substrates are sensitive and specific in *S. aureus* derived crude cell lysates.
Figure 2B:
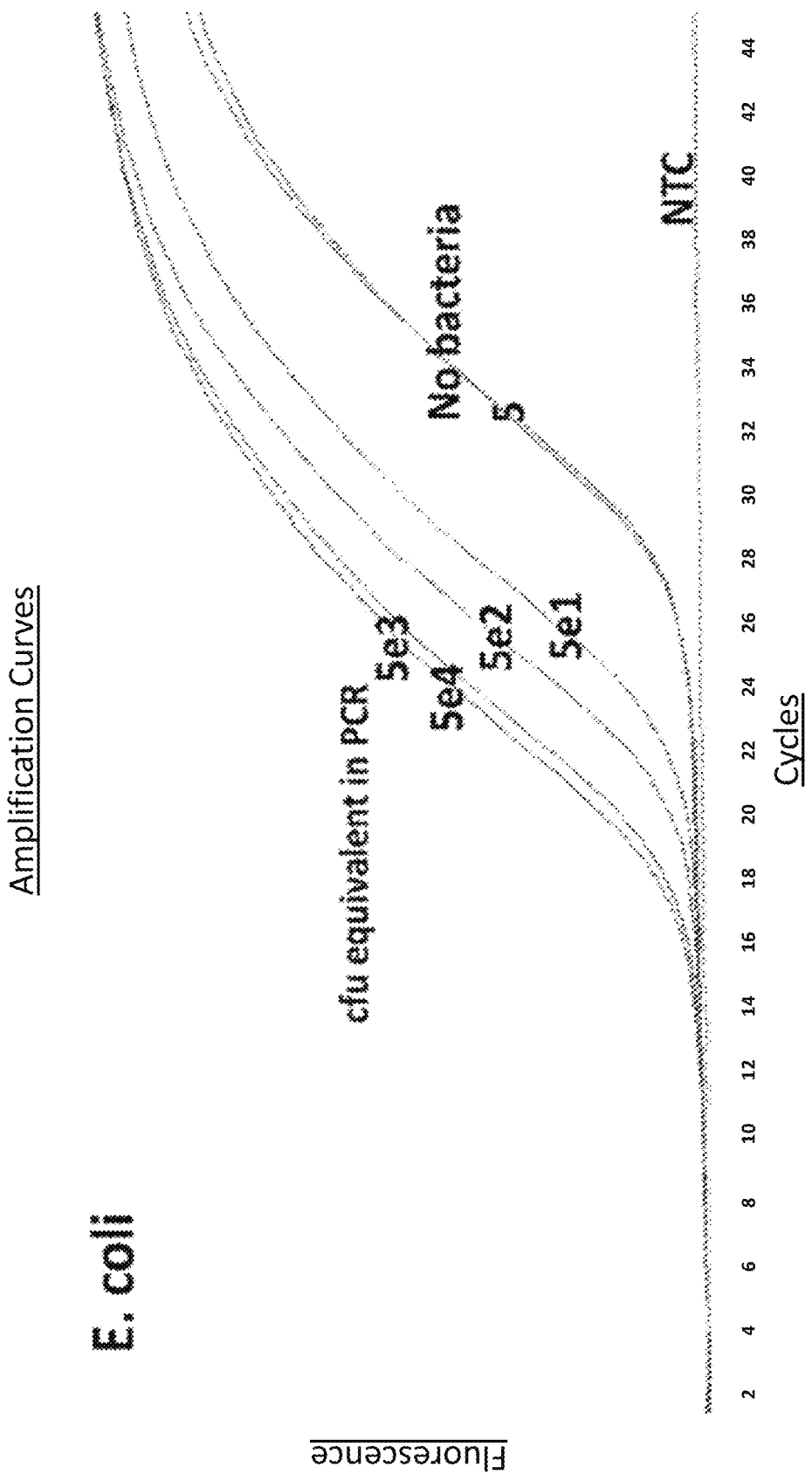
FIG. 2B. Graphical representation showing that Non-Ligate-able, Polymerase favorable substrates are sensitive and specific in *E. coli* derived crude cell lysate.
Figure 2C:
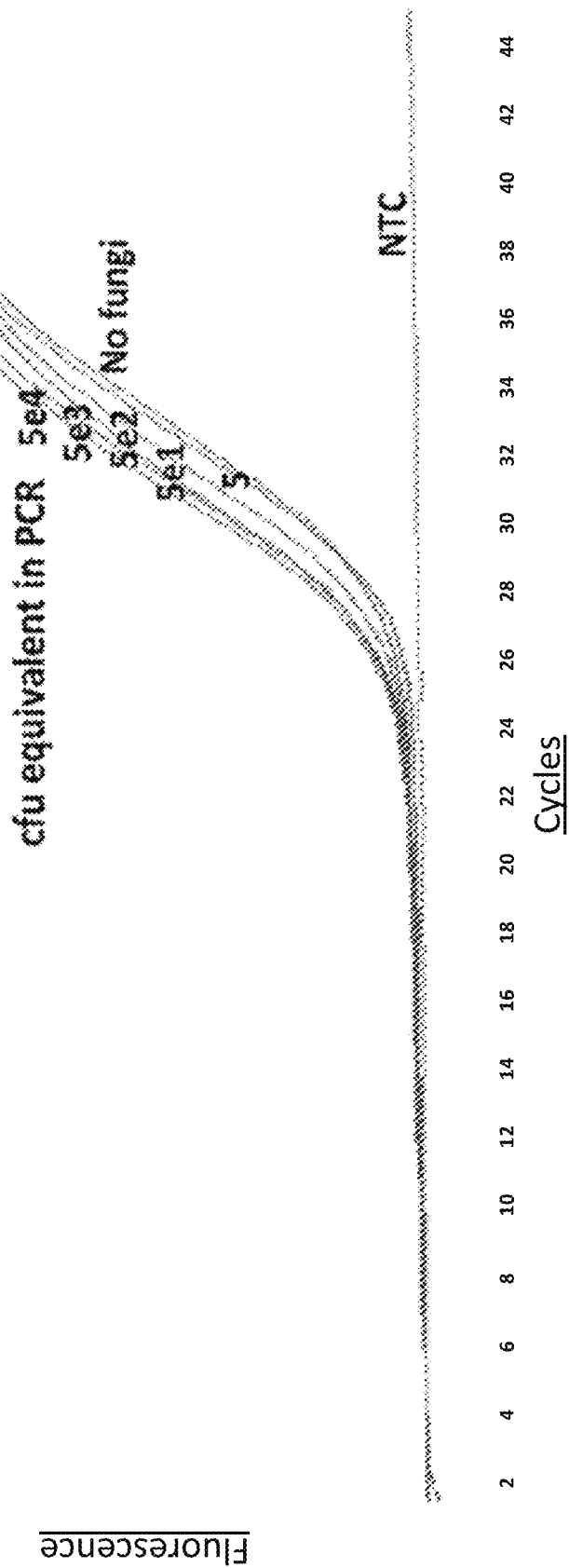
FIG. 2C. Graphical representation showing that Non-Ligate-able, Polymerase favorable substrates are sensitive and specific in *C. albicans* derived crude cell lysate.
Figure 2D:
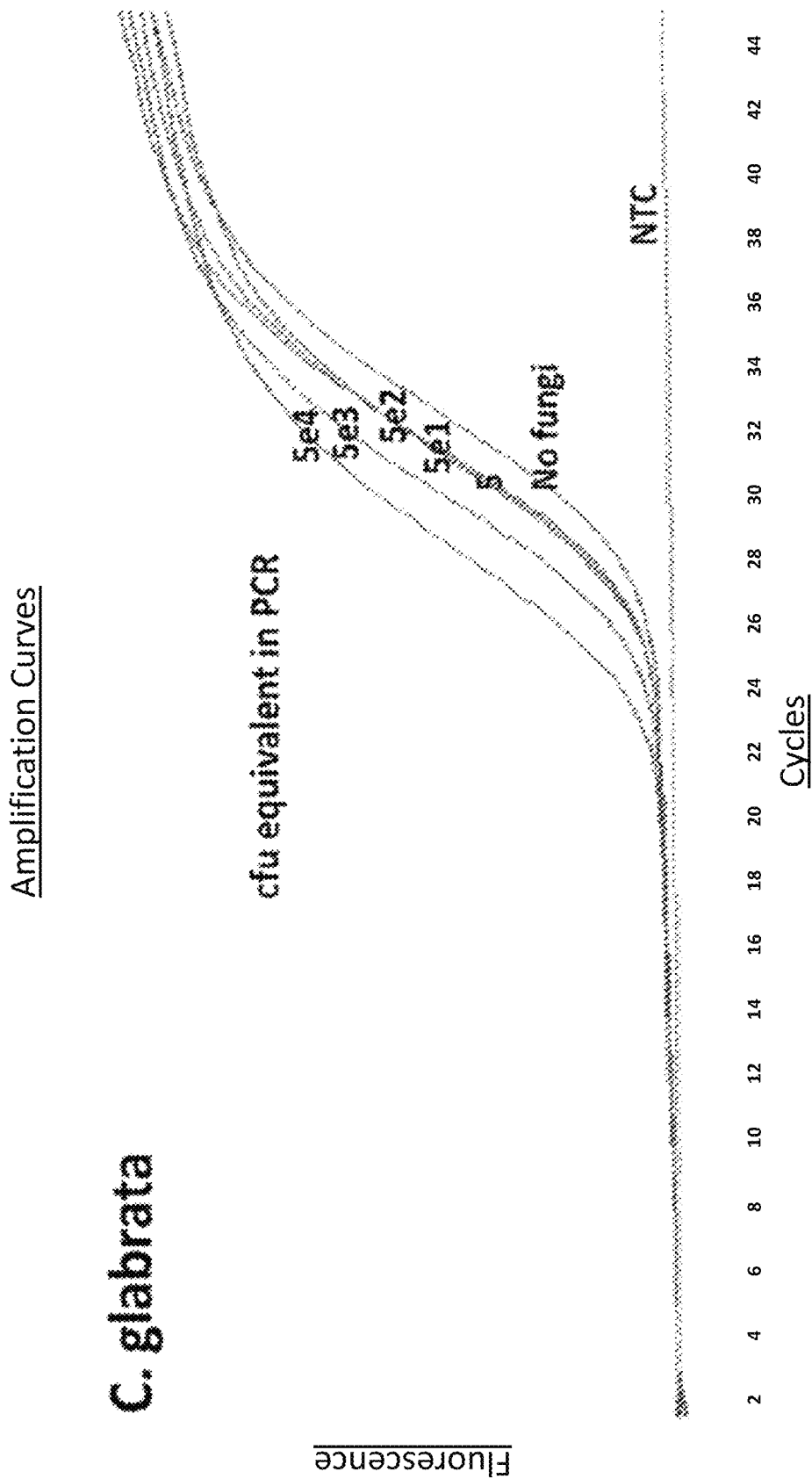
FIG. 2D. Graphical representation showing that Non-Ligate-able, Polymerase favorable substrates are sensitive and specific in *C. glabrata* derived crude cell lysate.

Thus, from the foregoing description it can be appreciated that the methods of the present invention are useful for identifying all microorganisms in which an enzyme, such as a suitable polymerase, is (or has been) expressed. In certain embodiments, the methods of the invention are applied to the detection of viable microorganisms and thus may be considered as a method for detecting a viable microorganism in a sample. In particular, in a preferred embodiment the methods of the invention may be useful for identifying bacteria or microorganisms in which the nucleic acid polymerase gene and its translated active protein polymerase is essential for viability. However, microorganisms, such as bacteria, recently rendered non-viable (for example through treatment with an anti-bacterial) may retain detectable polymerase activity until the enzyme is degraded.

In the development of the present invention, a paradigm shift in sample preparation of functional cellular biochemical components was discovered in that the present invention enables assays to be performed directly on samples from gently lysed cells, without the expensive complications added by traditional, and often extreme, denaturation based isolation protocols. Thus, it has been found that the present invention enables the detection of viable organisms in samples such as crude clinical lysates, including without limitation cell fractions from whole blood and or blood cultures, and from large volumes of the same, which are typically 10-20 ml, preferable in the range of 0.1-100 ml. The invention is particularly useful for the detection of all organisms associated with septicemia, and for those associated with conditions including but not limited to bacteremia, fungemia, and virus and parasitic conditions. It has unexpectedly been found that in accordance with the present invention detection of such organisms can be accomplished in such non-purified samples as described above, in contrast to the teachings of the conventional art in which sample derived polymerase inhibition, as well as the presence of interfering proteinases and nucleases, has been a barrier to such assay methods when performed on non-purified samples.

As described above, ligases, in particular NAD-dependent ligases, have been disclosed as a putatative useful indicator of the presence of a (viable) microorganism in a sample. However, in contrast, the present invention provides other viable microbe cell derived enzymes, useful rather than ligases, that can, similarly, be used to link their activity from viable cells to a high sensitivity signal generator such as amplification by techniques such as PCR and the like. This feature of the invention also potentially enables differentiating bacteria from fungi. In an example of an embodiment of the invention, the following may be used in this regard:
 a. Kinases add PO4 which could be used to enable a ligase or stop a polymerase
 b. Phosphates can be used to remove a PO4 and enable Polymerases
 c. DNA & RNA Polymerases can be used to extend substrates to enable downstream traditional PCR or isothermal amplifications
 d. Isothermal amplifications can be run off of endonuclease enzyme activities
 e. Ribosomes
 f. miRNA mechanisms
 g. Gyrase
 h. Helicase
 i. Exonucleases, 5'-3', 3'-5' i.e. removing a blocking groups such as PO4, TaqMan etc
 j. Endonucleases
 k. Proteases
 l. DNases
 m. RNases
 n. UDGlycosolases
 o. Repair enzymes In a preferred embodiment of the present invention, it has been discovered that measurement of DNA polymerase activity, in accordance with the invention, enables the determination of cell viability from microbe crude lysates. This may be verified using more selective modified oligo substrates in combination with very selective "hot starts" (as well known in the art) and controlling for RT, 37, 60C activities.

In one embodiment of the invention, the invention has application to blood product screening, especially of platelets as in this application any microbe growth is cause for discarding of product, and differentiation of bacteria from fungus is not necessary. In a further embodiment of the invention, phosphatases may be employed and are likely another excellent candidate enzyme to enable polymerase activity, as they remove either a 5' or 3' phosphate leaving an —OH— and thus could enable any polymerase by the removal of a designed 5' Taq included, or ligase (remove 3'). In addition, phosphatases are robust and may help to differentiate yeast and bacteria via optimization of pH. It will therefore be appreciated that any suitable enzyme that will enable polymerase as contemplated by the teachings herein may be useful in the practice of the present invention.

In the practice of the present invention, detection of microorganisms may include recently viable microorganisms, up until the point where DNA polymerase has been degraded, as appropriate. If a distinction between viable and recently viable microorganisms is required, a simple time course or comparison of polymerase activity between two or more time points, under appropriate conditions, should be sufficient to determine whether polymerase activity increases, persists or diminishes over time. In a preferred embodiment, if the polymerase activity is found to persist for, or increases over, an extended period or at (a) later time point (s) (compared to the initial measurement), this may indicate that the microorganisms are viable. If polymerase activity diminishes at (a) later time point (s), this may indicate that the detected activity was from recently viable microorganisms. This time course measurement approach may be especially useful when applied toward antibiotic susceptibility testing (AST) and as well as determination of other appropriate therapies. Detection methods are discussed in detail herein. In specific preferred embodiments of the invention, the microorganism is a bacterium, as herein described, and the methods of the invention may be more generally applicable (Wilkinson et al., Molecular Microbiology (2001) 40(6), 1241-1248). The bacteria may, as well, be mesophillic and/or thermophillic bacteria, for example.

A "sample" in the context of the present invention is defined to include any sample in which it is desirable to test for the presence of a microorganism, in particular a bacterium. Thus the sample can consist of a clinically provided crude microbe lysate, or may comprise a clinical sample of blood or blood culture, or comprise a sample suitable for an in vitro assay system, for example. Samples may also comprise beverage or food samples or preparations thereof, or pharmaceutical or cosmetic products such as personal care products including shampoos, conditioners, moisturizers etc., all of which are tested for microbial contamination as a matter of routine. The sample may comprise tissue or cells and may comprise sputum or or a platelet sample. In addition, the methods and kits of the invention may be used to monitor contamination of surfaces, such as for example in locations where food is being prepared. In a preferred embodiment, contamination is indicated by the presence of polymerase activity. The contamination may be from any microbial source, in particular bacterial contamination. Furthermore, the invention is also useful in monitoring environmental conditions such as water supplies, wastewater, marine environments etc. The invention is also useful in monitoring bacterial growth in fermentation procedures and in air sampling where bacteria or spore content can be assessed in hospital, industrial facilities or in biodefense applications.

The methods of the invention rely on the fact that if there are one or more (viable) micro-organisms, in particular bacteria, present in the sample, enzyme activity, preferably DNA polymerase activity, will be present. The enzyme can thus, under appropriate conditions, catalyse a reaction to generate a novel detectable nucleic acid molecule (in a subsequent process). The novel nucleic acid molecule may be detected by any suitable means such as hereinafter described, thereby allowing a determination of the presence of the microorganisms in the sample under test.

Thus, if the microorganism is not present in the sample, there will be no enzyme (e.g., polymerase) activity in the sample and thus the novel detectable nucleic acid molecule will not be generated.

The methods of the present invention provide significant technical advantages, due in large part to the fact that a novel nucleic acid molecule is generated as part of the method. In the methods of the present invention, unreacted nucleic acid molecule will not contribute to the signal, and as a result no false positive signals should be produced when the methods are carried out.

Furthermore, the methods provided by the invention are highly sensitive, and may provide detection of the enzyme (e.g., polymerase) present in the sample down to femtogram and possibly even attogram levels. The sensitivity is derived from the fact that every bacterial cell contains thousands of enzyme molecules, and thus each can catalyse multiple events under suitable conditions. Unlike direct PCR approaches, which must target one or a few copies of a gene per cell or use additional steps or reagents to detect ribosomal or messenger RNA, the approach described herein targets the detection of multiple copies of the enzyme per cell in a simple assay format.

As stated herein, the first step in a method according to the invention comprises contacting the sample with a nucleic acid molecule which acts as a substrate for the enzyme, for example polymerase, activity in the sample.

Suitable substrate nucleic acid molecules for use in the invention are described in more detail below. The nucleic acid molecules may incorporate synthetic nucleotide analogues as appropriate or may be RNA or DNA based for example, or mixtures thereof. They may be labelled, such as using a fluorescent label, or FRET pair, in certain embodiments to facilitate detection. Suitable detection methods are described herein.

"Nucleic acid" is defined herein to include any natural nucleic acid and natural or synthetic analogues that are capable of generating a detectable nucleic acid molecule by the action of polymerase. Suitable nucleic acid molecules may be composed of, for example, double or single-stranded DNA and double or single-stranded RNA.

Though the nucleic acid substrate may comprise a blunt-ended double-stranded DNA molecule, in an embodiment of the invention the nucleic acid substrate for the polymerase comprises two double stranded DNA molecules with a complementary overhang and 5' phosphate groups at the ends to be joined. In one specific embodiment, the complementary overhang is between 2 and 10, such as 3 or 5 base pairs. In an alternative embodiment, the nucleic acid substrate comprises a DNA molecule with a nick containing a 5' phosphate. Synthesized nucleic acid molecules are commercially available and can be made to order with a terminal 5$^1$ phosphate group attached. This has the technical advantage that 100% of the nucleic acid molecules used in the methods of the invention will be labeled with a 5' phosphate group.

In especially preferred embodiments of the invention, if polymerase is present in the sample, it will catalyse and a novel nucleic acid molecule (incorporating an overall novel sequence) will be formed which can be detected by a subsequent process, as detailed herein (such as PCR for example).

Thus, the substrate nucleic acid molecule may, in fact, comprise two or more nucleic acid molecules as appropriate. This applies generally to the methods and kits of the invention.

In certain embodiments, the nucleic acid substrate comprises two double stranded nucleic acid molecules with single-stranded complementary overhangs.

It is to be appreciated that the novel methods of the present invention can be used to differentiate ligase from polymerase by taking a sample suspected of containing both and testing for both polymerase and ligase in parallel in separate reaction vessels, then subtracting the signals, thus in fact determining the true ligase levels found in the sample. This can be represented by the following equation:

[polymerase signal−ligase signal (polymerase+ligase)=true ligase signal]

It also is to be appreciated that in any embodiment of the present invention, the action of polymerases on nucleic acids is well known and thus it can be seen that many different types of nucleic acid substrates can be selected for use and will have the advantages of utilization in the novel methods of the invention, as herein described. Preferably, the nucleic acid substrate is present in excess, and in particular in large molar excess, over the polymerase in the sample. This is an important technical distinction over prior art methods. Because a novel polymerized nucleic acid molecule is detected, only the presence of this molecule in the sample is essential for the detection methods to work effectively. Thus, it is not detrimental to the methods of the invention if other nucleic acid molecules are present in the sample such as from the bacteria to be detected or from mammalian or fungal sources which may be found in the sample to be tested for example.

The present invention can be more fully described by reference to the following examples of experimental work conducted in accordance with the invention. Also, while certain of the preferred embodiments of the present invention have been described and specifically exemplified above, it is not intended that the invention be limited to such embodiments.

Example 1

Discovery of a Ligase Independent Mechanism

Three different DNA substrates (A) were incubated with *E. coli* ligase or no ligase and subjected to PCR containing full length DNA ligase substrate specific PCR primers in the presence/absence of UNG. PCR was monitored via SYBR green (qPCR) and the resultant reactions were subjected to gel analysis (B). Three different DNA substrates (A) were incubated with *E. coli* ligase or no ligase and subjected to PCR containing S1-Extension detection primers in the presence/absence of UNG. PCR was monitored via the commercially—available Zeus-Probe (qPCR) methodology (Zeus Scientific, Inc., Raritan, N.J.) and the resultant reactions were subjected to gel analysis (C). Decreasing amounts of a non-ligatable DNA substrate (S1/AS only) was incubated with three different commercially available DNA polymerases and subjected to Zeus-Probe qPCR analysis. The results of these experiments are illustrated graphically in FIG. 1.

Example 2

Non-Ligate-able, Polymerase Favorable Substrates Were Found To Be Sensitive and Specific in Microbe Derived Crude Cell Lysates Decreasing amounts microbes were beadmill-lysed and incubated with a DNA substrate (S1/AS only) in the presence of DNA polymerase buffer and dNTP's at 37° C. for 30 min. (A). The lysates were then subjected to Zeus-Probe qPCR containing S1-extension specific primers. The results are displayed graphically in FIG. 2.

Example 3

Figure 3:
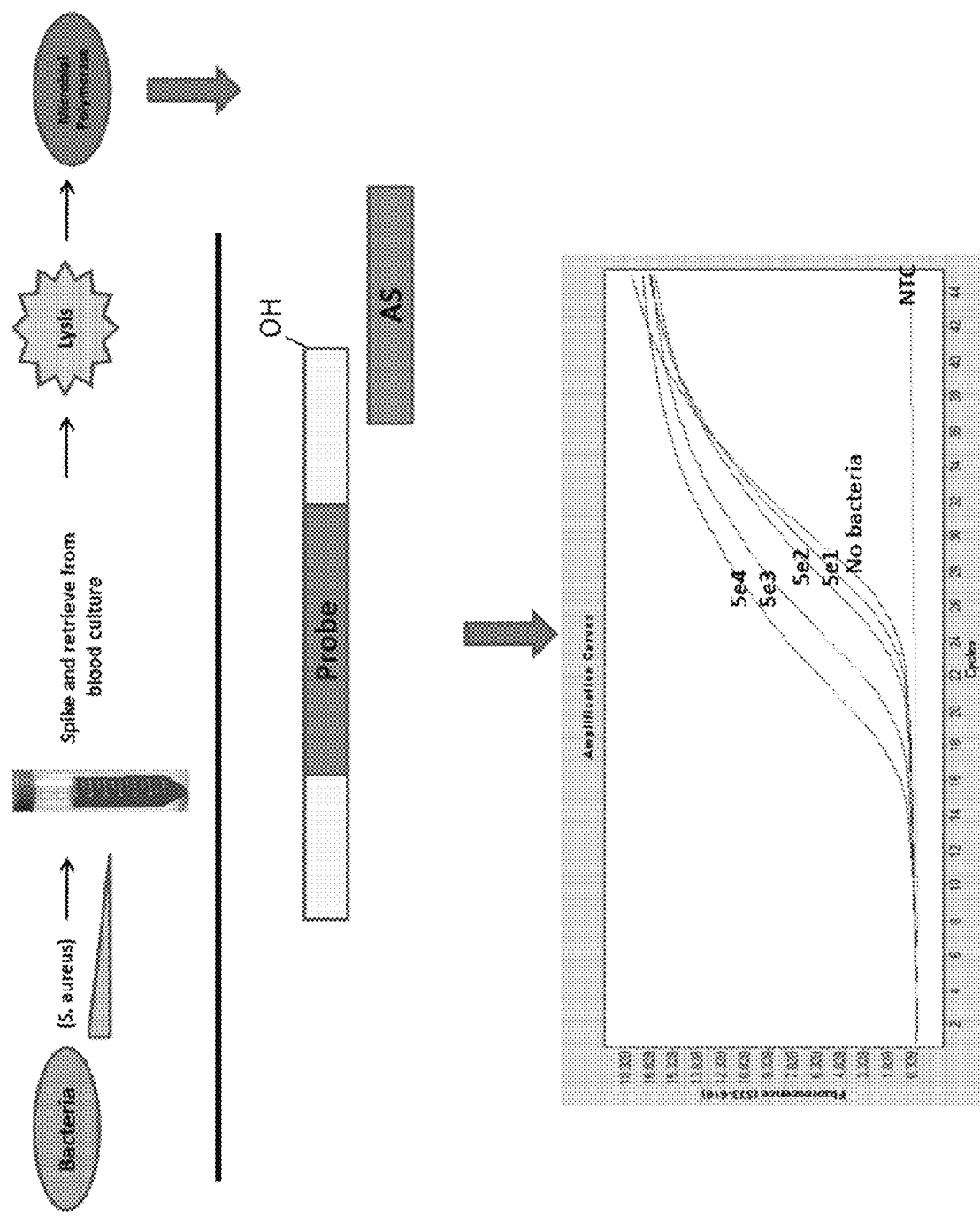
FIG. 3 is a graphical representations showing Non-Ligate-able, Polymerase favorable substrates are sensitive and specific in Microbe Spiked Blood Culture derived crude cell lysates.

Non-Ligate-able, Polymerase Favorable Substrates Were Found To Be Sensitive and Specific in Microbe Spiked Blood Culture Derived Crude Cell Lysates Decreasing amounts microbes were spiked into 10 ml of blood broth. The microbes were subsequently recovered, subjected to beadmill-lysis and incubated with a DNA substrate (S1/AS only) in the presence of DNA polymerase buffer and dNTP's at 37° C. for 30 min. (A). The lysates were then subjected to Zeus-Probe qPCR containing S1-extension specific primers. The results are displayed graphically in FIG. 3.

Accordingly, in yet another aspect the present invention improves upon the invention described and claimed in WO/2009/007719. In accordance with the present invention, it has been discovered that the putative DNA ligase specific substrate in accordance with the disclosure of said WO/2009/007719 yields robust signals from either purified DNA polymerase or purified DNA ligase, such that the methods set forth therein are not rendered DNA ligase specific when applied to the intended sample type, such as septicemia samples. For example, in the development of the present invention, septicemia samples using the sample preparation methods taught by WO/2009/007719 were input into the assay protocols as taught therein as crude microbe cell lysates containing a high abundance of DNA polymerases. DNA polymerase(s) are abundant in all living cells. It was found that the assays as disclosed in WO/2009/007719 are incapable of discriminating between any DNA polymerase and DNA ligase derived signals, when inputting non-ligase-purified samples, which from a practical standpoint include all clinical sample inputs, because isolating ligase is neither a practical nor routine procedure as disclosed in this reference, when attempting to obtain results from clinical samples. Rather, experiments conducted in accordance with what is taught by this reference were found to produce an assay signal contaminated by DNA polymerase, not a DNA ligase specific signal, which is clearly the desired result in accordance with this reference.

These findings described above are contrary to the ability of a system, produced in accordance with the teachings of WO/2009/007719, to specifically detect DNA ligase from viable cells. It further precludes the intended ability of the disclosed assay of this reference to differentiate viable cell-derived NAD dependent bacterial ligase from ATP dependent fungal ligase, as active polymerases are common to all viable cells and cannot be differentiated from any ligases in such an assay system. Having thus identified this critical problem, which is clearly unanticipated by this reference or any other known art, the present invention provides improvements which enable specific ligase signals to be detected from non-purified ligase samples, such as crude microbe lysates, by providing alternative, substitute DNA substrates, as hereinafter described, that do not allow interfering signals from DNA polymerases to be detected.

The present invention therefore also provides improved methods, and compositions and kits based thereon, of detecting an enzyme selected from the group consisting of NAD-dependent ligase, or phosphatase, or a mixture thereof as an indicator of the presence of a microorganism in a sample, the methods comprising:

(a) contacting the sample with a nucleic acid molecule which acts as a substrate for enzyme activity in the sample, while not allowing interfering signals from DNA polymerase, (b) incubating the thus contacted sample under conditions suitable for enzyme activity; and (c) determining the presence (and/or the amount) of an enzyme modified nucleic acid molecule resulting from the action of the selected enzyme or mixture on the substrate nucleic acid molecule to indicate the presence of the microorganism.

Thus, the improved methods of the invention are useful for identifying all microorganisms in which an NAD-dependent ligase, or a phosphatase, or mixtures thereof, are (or have been) expressed.

In a preferred embodiment of the invention the first step in the improved method disclosed herein comprises contacting the sample with a nucleic acid molecule which acts as a substrate for NAD-dependent ligase activity in the sample, while not allowing interfering signals from DNA polymerase. Any suitable enzyme modified, or ligatable, molecule which can be specifically detected, once ligated, may be utilized in the methods of the invention.

The substrate nucleic acid molecules for use in the methods, and inclusion in the kits, of the present invention, must be of sequence and structure such that the NAD-dependent ligase can act on the molecule to produce a detectable enzyme modified or ligated (novel) nucleic acid molecule, and such that it does not allowing interfering signals from DNA polymerase.

It is to be appreciated that in the development of the present invention, it was noted that the elimination of the polymerase chain reaction (PCR) Taq-DNA polymerase derived background was not a viable solution to the lack of specificity that has been found in the current substrate design as disclosed in WO/2009/007719, as it was determined to be a separate detection system issue that would have to be addressed separately and is therefore outside the scope of the present disclosure.

Accordingly, in the present case for experiments leading up to the present invention it was specifically set as a goal to block all DNA polymerase activity with a inhibitor additive that does not interfere with ligase. In order to accomplish this, it was noted that DNA polymerases have well-documented enzyme functions that need to be neutralized/controlled:

(a) 5'-3' DNA polymerase activity
(b) 3'-5'exonuclease activity
(c) 5'-3'exonuclease activity
(d) inherent esterase activity It has been determined in accordance with the present invention that suitable substrate nucleic acid molecule strategies for use in the novel methods of the present invention, which are suitable in substitution for those substrate molecules disclosed as being used in the methods of WO/2009/007719, may include, but are not limited to, the following:

1. Modified nucleotides that inhibit the polymerase from any activity
2. Dideoxynucleotides ddCTP, ddGTP that stop the polymerase upon first base addition and sequester-neutralize its activity while ligase enjoys productive reactions using dATP
3. Dideoxyoligonucleotides that prevent AS oligo from being extended
4. S1 oligos with polymerase inhibition modified bases incorporated to block their activity on this DNA substrate 5. DNA polymerase specific antibodies that inhibit this activity—these are well known in the art of PCR
6. Aptamer oligo inhibitory complexes.
7. DNA substrate hybridization strategies that eliminate polymerase extended substrates from being detected in downstream amplifications such as PCR—by shortening AS on the 5' side combined with a true "Hot Start," as such term is known in the art
8. DNA substrate hybridization strategies that eliminate polymerase from binding and extending by shortening AS on 3' side but do not effect ligase
9. Relative rate kinetics combined with polymerase extension length balanced in favor of ligase.
10. Per-PCR S1 3'-dideoxy competition (full length, or a 13mer that is the complementary to the 3' of the AS)
11. Pre-PCR S1 3' Phosphate competition
12. Complete removal of AS using optimal UNG (standard UNG enzyme) conditions
13. Complete removal of AS using Thermostable UNG (NEB). Will enable heat treatment of UNG to eliminate contaminating ligase/polymerase, PCR mm must have dTTP
14. Make an AS that has deoxyuridine (UNG removal) and the rest RNA bases to allow UNG/Rnase co-treatment prior to PCR
15. Need to get dideoxy 3' AS
16. Shorten the 3' end of the AS to reduce Taq docking at higher temps (i.e. 65 deg)
17. AS covalently attached to a solid support during ligation/extension step
18. 3'-dideoxy S2 reverse complement (full length, or maybe just a 13mer that is the complementary to the S1 Pol extension)
19. For background reduction—"Hot Start" strategies, as well known in the art—100% elimination of unwanted oligo or extended oligo hybridizations.
   a. True Physical—not easy to do as all contact materials must be at the hot temperature of about 90 degrees C., and must never drop below a threshold temperature of about 65 degrees C., the problem being that the transfer process creates a temperature drop, which should be avoided.
   b. Non enzyme Hot Starts, e.g., drop in 2 mM MgCl (0.1 mM EDTA protected), primers, dNTPs or other essential components.
   c. Chem—primer Hot Start.

Although it has been shown that the improvements of the present invention can be realized by the substitution of the suitable substrate nucleic acid molecules described herein for those described in WO/2009/007719, it is to be appreciated that the present invention is not to be limited in scope by the specific embodiments described herein. Indeed, various modifications of the invention in addition to those described herein will become apparent to those skilled in the art from the foregoing description. All such modifications are intended to fall within the scope of the present invention. Moreover, all embodiments described herein are considered to be broadly applicable and combinable with any and all other consistent embodiments, as appropriate.

It will be appreciated by those of ordinary skill in the art that the broad fundamental principles and teachings of the present invention are capable of being applied to optimize all variations of denaturant-enabled-crude lysate (bead mills & ultrasonics)-direct-probe/SYBR-PCR analysis of various biological tissue samples (including, but not limited to, blood, body fluid, and soft tissues) for not only microorganisms or microbes as specifically described above, but also for various pathogens, such as any bacteria, fungi, virus, parasites, etc.

Although specific references are made herein to PCR, It is further to be appreciated that the improvements of the present invention are not limited to PCR or similar methodologies. Amplification assays contemplated for use in the present invention include, but are not limited to, other well-known nucleic-acid based techniques such as DNA amplification assays, PCR assays incorporating thermostable polymerases, and isothermal amplifications methods. It is to be appreciated that one skilled in the art may conceive of various suitable amplification methods that will be useful in the practice of the present invention, and that therefore the invention is not intended to be limited thereby.

It is also to be appreciated that the present invention has applications in any and all methods, procedures and processes involving DNA diagnostics. Examples of such applications include but are not limited to those involving food, water safety, bioterrorism, medical/medicines and/or anything involving pathogen detection. In the food industry, the present invention can be used to monitor the efficacy of preservatives. The method of the invention has the potential to be applied to all cells. Although bacterial cells are exemplified in the example, one of ordinary skill in the art can easily see that the methods of the invention can be applied to many other cell types. The invention can also be used for the identification of substances that can disrupt membranes and/or kill cells, e.g. bacterial cells. The identification of new disinfectants and/or antibiotics are now a priority since multidrug resistance organisms have flourished and spread in health institutions and patients.

It will further be appreciated that the methods of the invention, in combination with quantitative PCR as a tool, can quickly and successfully identify the impact of a disinfectant and/or antibiotic without having to spend time culturing the cells and waiting for growth. In some instances, organisms can take days to weeks to culture, and thus it can take significant time to see if the candidate substance has been able to kill cells, like microorganisms. In other instances, certain organisms will not grow in cell culture, therefore making it difficult to determine if a substance was effective. Thus, applying the novel methods of the invention can save time and resources for identification of novel disinfectants and/or antibiotics.

A further advantage of the novel methods according to the invention is their ease of use. For example, using these methods, large amounts of samples can easily be tested for the presence of viable cells, e.g. bacteria. For example, samples may be tested for the presence of potentially live bacteria with intact cell membranes. In another embodiment, environmental samples may be tested for the presence of viable cells, e.g. bacteria. These samples may be, for example, collected from soil or be parts of plants. The methods according to the invention can further be used for testing of treated waste water both before and after release.

The methods according to the invention may further be used for testing medicinal samples, e.g., stool samples, blood cultures, sputum, tissue samples (also cuts), wound material, urine, and samples from the respiratory tract, implants and catheter surfaces.

Another field of application of the methods according to the invention can be the control of foodstuffs. In other embodiments, the food samples are obtained from milk or milk products (yogurt, cheese, sweet cheese, butter, and buttermilk), drinking water, beverages (lemonades, beer, and juices), bakery products or meat products. The method of the invention can determine if preservatives in the food or antimicrobial treatment of food (such as pasteurization) has prevented cell growth. A further field of application of the method according to the invention is the analysis of pharmaceutical and cosmetic products, e.g. ointments, creams, tinctures, juices, solutions, drops, etc.

In addition, the methods of the invention can identify potentially viable members of a microbial community for ecological studies, health of specific soils for agricultural and/or ecological systems. Traditionally identifying a bacterial community has been performed using cultivation-based approaches or plate counts. The more colonies that are counted, the more bacteria are estimated to be in the original sample. Problems, however, arise from sometimes long incubation times (in the range of days) making this method unsuitable for timely and accurate results. These drawbacks are utilizing the methods of the invention.

Non-limiting examples of bacteria that can be subjected to analysis using the methods of the invention or to detect potential viability in a sample using the method of the invention comprise, for example: *B. pertussis, Leptospira pomona, S. paratyphi* A and B, *C. diphtheriae, C. tetani, C. botidinum, C. perfringens, C. feseri* and other gas gangrene bacteria, *B. anthracis, P. pestis, P. multocida, Neisseria meningitidis, N. gonorrheae, Hemophilus influenzae, Actinomyces* {e.g., *Norcardia*), *Acinetobacter,* Bacillaceae {e.g., *Bacillus anthrasis*), *Bacteroides* {e.g., *Bacteroides fragilis*), *Blastomycosis, Bordetella, Borrelia* {e.g., *Borrelia burgdorferi*), *Brucella, Campylobacter, Chlamydia, Coccidioides, Corynebacterium* {e.g., *Corynebacterium diptheriae*), *E. coli* {e.g., Enterotoxigenic *E. coli* and Enterohemorrhagic *E. coli*), *Enterobacter* (e.g. *Enterobacter aerogenes*), Enterobacteriaceae (*Klebsiella, Salmonella* (e.g., *Salmonella typhi, Salmonella enteritidis, Serratia, Yersinia, Shigella*), *Erysipelothrix, Haemophilus* (e.g., *Haemophilus influenza* type B), *Helicobacter, Legionella* (e.g., *Legionella pneumophila*), *Leptospira, Listeria* (e.g., *Listeria monocytogenes*), *Mycoplasma, Mycobacterium* (e.g., *Mycobacterium leprae* and *Mycobacterium tuberculosis*), *Vibrio* (e.g., *Vibrio cholerae*), Pasteurellacea, *Proteus, Pseudomonas* (e.g., *Pseudomonas aeruginosa*), Rickettsiaceae, Spirochetes (e.g., *Treponema* spp., *Leptospira* spp., *Borrelia* spp.), *Shigella* spp., Meningiococcus, Pneumococcus and all *Streptococcus* (e.g., *Streptococcus pneumoniae* and Groups $A_3$ B, and C Streptococci), Ureaplasmas. *Treponema pollidum, Staphylococcus aureus, Pasteurella haemolytica, Corynebacterium diptheriae* toxoid, Meningococcal polysaccharide, *Bordetella pertusis, Streptococcus pneumoniae, Clostridium tetani* toxoid, and *Mycobacterium bovis*. The above list is intended to be merely illustrative and by no means is meant to limit the invention to detection to those particular bacterial organisms.

A particularly preferred embodiment of the present invention utilizes PCR. General procedures for PCR are taught in U.S. Pat. No. 4,683,195 (Mullis, et al.) and U.S. Pat. No. 4,683,202 (Mullis, et al.). However, optimal PCR conditions used for each amplification reaction are generally empirically determined or estimated with computer software commonly employed by artisans in the field. A number of parameters influence the success of a reaction. Among them are annealing temperature and time, extension time, $Mg^{2+}$, pH, and the relative concentration of primers, templates, and deoxyribonucleotides. Generally, the template nucleic acid is denatured by heating to at least about 95° C. for 1 to 10 minutes prior to the polymerase reaction. Approximately 20-99 cycles of amplification are executed using denaturation at a range of 90° C. to 96° C. for 0.05 to 1 minute, annealing at a temperature ranging from 48° C. to 72° C. for 0.05 to 2 minutes, and extension at 68° C. to 75° C. for at least 0.1 minute with an optimal final cycle. In one embodiment, a PCR reaction may contain about 100 ng template nucleic acid, 20 uM of upstream and downstream primers, and 0.05 to 0.5 mm dNTP of each kind, and 0.5 to 5 units of commercially available thermal stable DNA polymerases.

A variation of the conventional PCR is reverse transcription PCR reaction (RT-PCR), in which a reverse transcriptase first coverts RNA molecules to single stranded cDNA molecules, which are then employed as the template for subsequent amplification in the polymerase chain reaction. Isolation of RNA is well known in the art. In carrying out RT-PCR, the reverse transcriptase is generally added to the reaction sample after the target nucleic acid is heat denatured. The reaction is then maintained at a suitable temperature (e.g. 30-45° C.) for a sufficient amount of time (10-60 minutes) to generate the cDNA template before the scheduled cycles of amplification take place. One of ordinary skill in the art will appreciate that if a quantitative result is desired, caution must be taken to use a method that maintains or controls for the relative copies of the amplified nucleic acid. Methods of "quantitative" amplification are well known to those of skill in the art. For example, quantitative PCR can involve simultaneously co-amplifying a known quantity of a control sequence using the same primers. This provides an internal standard that may be used to calibrate the PCR reaction.

Another alternative of PCR is quantitative PCR (qPCR). qPCR can be run by competitive techniques employing an internal homologous control that differs in size from the target by a small insertion or deletion. However, non-competitive and kinetic quantitative PCR may also be used. Combination of real-time, kinetic PCR detection together with an internal homologous control that can be simultaneously detected alongside the target sequences can be advantageous.

Primers for PCR, RT-PCR and/or qPCR are selected within regions or specific bacteria which will only amplify a DNA region which is selected for that specific organism. Alternatively, primers are selected which will hybridize and amplify a section of DNA which is common for all organisms. Primer selection and construction is generally known in the art. In general, one primer is located at each end of the sequence to be amplified. Such primers will normally be between 10 to 35 nucleotides in length and have a preferred length from between 18 to 22 nucleotides. The smallest sequence that can be amplified is approximately 50 nucleotides in length (e.g., a forward and reverse primer, both of 20 nucleotides in length, whose location in the sequences is separated by at least 10 nucleotides). Much longer sequences can be amplified. One primer is called the "forward primer" and is located at the left end of the region to be amplified. The forward primer is identical in sequence to a region in the top strand of the DNA (when a double-stranded DNA is pictured using the convention where the top strand is shown with polarity in the 5' to 3' direction). The sequence of the forward primer is such that it hybridizes to the strand of the DNA which is complementary to the top strand of DNA. The other primer is called the "reverse primer" and is located at the right end of the region to be amplified. The sequence of the reverse primer is such that it is complementary in sequence to, i.e., it is the reverse complement of a sequence in, a region in the top strand of the DNA. The reverse primer hybridizes to the top end of the DNA. PCR primers should also be chosen subject to a number of other conditions. PCR primers should be long enough (preferably 10 to 30 nucleotides in length) to minimize hybridization to greater than one region in the template. Primers with long runs of a single base should be avoided, if possible. Primers should preferably have a percent G+C content of between 40 and 60%. If possible, the percent G+C content of the 3' end of the primer should be higher than the percent G+C content of the 5' end of the primer. Primers should not contain sequences that can hybridize to another sequence within the primer (i.e., palindromes). Two primers used in the same PCR reaction should not be able to hybridize to one another. Although PCR primers are preferably chosen subject to the recommendations above, it is not necessary that the primers conform to these conditions. Other primers may work, but have a lower chance of yielding good results.

PCR primers that can be used to amplify DNA within a given sequence can be chosen using one of a number of computer programs that are available. Such programs choose primers that are optimum for amplification of a given sequence (i.e., such programs choose primers subject to the conditions stated above, plus other conditions that may maximize the functionality of PCR primers). One computer program is the Genetics Computer Group (GCG recently became Accelrys) analysis package which has a routine for selection of PCR primers.

The oligonucleotide primers and probes disclosed below can be made in a number of ways. One way to make these oligonucleotides is to synthesize them using a commercially-available nucleic acid synthesizer. A variety of such synthesizers exists and is well known to those skilled in the art.

Nucleic acid may also be detected by hybridization methods. In these methods, labeled nucleic acid may be added to a substrate containing labeled or unlabeled nucleic acid probes. Alternatively, unlabeled or unlabeled nucleic acid may be added to a substrate containing labeled nucleic acid probes. Hybridization methods are disclosed in, for example, Micro Array Analysis, Marc Schena, John Wiley and Sons, Hoboken N.J. 2003.

Methods of detecting nucleic acids can include the use of a label. For example, radiolabels may be detected using photographic film or a phosphoimager (for detecting and quantifying radioactive phosphate incorporation). Fluorescent markers may be detected and quantified using a photodetector to detect emitted light (see U.S. Pat. No. 5,143,854 for an exemplary apparatus). Enzymatic labels are typically detected by providing the enzyme with a substrate and measuring the reaction product produced by the action of the enzyme on the substrate. Colorimetric labels are detected by simply visualizing the colored label. In one embodiment, the amplified nucleic acid molecules are visualized by directly staining the amplified products with a nucleic acid-intercalating dye. As is apparent to one skilled in the art, exemplary dyes include but not limited to SYBR green, SYBR blue, DAPI, propidium iodine, and ethidium bromide. The amount of luminescent dyes intercalated into the amplified DNA molecules is directly proportional to the amount of the amplified products, which can be conveniently quantified using a conventional detection devices according to manufacturers' instructions. A variation of such an approach is gel electrophoresis of amplified products followed by staining and visualization of the selected intercalating dye. Alternatively, labeled oligonucleotide hybridization probes (e.g. fluorescent probes such as fluorescence resonance energy transfer (FRET) probes and colorimetric probes) may be used to detect amplification. Where desired, a specific amplification of the genome sequences representative of the biological entity being tested, may be verified by sequencing or demonstrating that the amplified products have the predicted size, exhibit the predicted restriction digestion pattern, or hybridize to the correct cloned nucleotide sequences.

The present invention also comprises kits. For example, the kit can comprise a substrate containing a nucleic acid molecule for activity of the selected enzyme or mixture in the sample (while not allowing interfering signals from DNA polymerase), incubation means for incubating the sample and substrate under conditions suitable for enzyme activity, and means for specifically determining the presence (and/or the amount) of a nucleic acid molecule resulting from the action of the selected enzyme or mixture on the substrate nucleic acid molecule (as an indication of the presence of the microorganism). Such a kit can also comprise other reagents suitable for conducting the novel methods of the invention, for screening normally sterile body fluids for the presence of absence of microorganisms therein and to provide diagnostic, prognostic patient management information, as well as primers useful for amplifying nucleic acid molecule corresponding to organisms specifically or generally, buffers and reagents for isolating DNA, and reagents for PCR. The kit can further include detectably labeled oligonucleotide, which hybridizes to a nucleic acid sequence encoding a polypeptide corresponding to organisms of interest. The kit can also contain a control sample or a series of control samples which can be assayed and compared to a test sample contained. Each component of the kit can be enclosed within an individual container and all of the various containers can be within a single package, along with instructions for interpreting the results of the assays performed using the kit.

It is also to be appreciated that the methods provided by the invention further comprise conducting a complete or partial microorganism genome and or transcriptome sequence analysis utilizing the principles and teachings provided herein, and wherein the complete or partial microorganism genome and or transcriptome sequence analysis can be performed simultaneously, in concert, or in parallel using a single sample preparation as herein described. It is also to be appreciated that the novel methods herein of the invention can provide for the diagnostic measure and detection of agents with anti-microbial and or anti-polymerase activity, useful in the management of patients.

The contents of all references, patents and published patent applications cited throughout this application, are incorporated herein by reference to the same extent as if each individual publication, patent or patent application was specifically and individually indicated to be incorporated by reference.

The foregoing detailed description has been given for clearness of understanding only and no unnecessary limitations should be inferred therefrom as modifications will be obvious to those skilled in the art. It is not an admission that any of the information provided herein is prior art or relevant to the presently claimed inventions, or that any publication specifically or implicitly referenced is prior art.

Unless defined otherwise, all technical and scientific terms used herein have the same meaning as commonly understood by one of ordinary skill in the art to which this invention belongs.

Although the present invention has been described in detail, the specific examples herein are provided by way of specific illustration of embodiments of the invention and for purposes of clarity of understanding. It will be readily apparent to those of ordinary skill in the art, in light of the teachings of this invention as set forth herein, that many changes and modifications may be made to these embodiments thus described without departing from the spirit or scope of the invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

We claim:

1. A method for detecting the presence of a bacterium or a fungus in a sample, wherein DNA polymerase activity is detected as an indicator of the presence of said bacterium or fungus in said sample, which method comprises:
    (a) preparing the sample using a differential cell lysis sample preparation method, thereby allowing for only bacterium or fungi derived DNA polymerase activity to modify a DNA polymerase substrate;
    (b) contacting the prepared sample of (a) with a nucleic acid molecule which acts as a substrate for DNA polymerase activity in the prepared sample, wherein the substrate is a partially double-stranded DNA substrate consisting of a sense strand DNA oligonucleotide and an antisense strand DNA oligonucleotide, wherein the sense strand DNA oligonucleotide and the antisense strand DNA oligonucleotide overlap to form a double-stranded region and a single-stranded portion of the antisense strand acts as a template with the sense strand of the double-stranded region acting as a primer to create an extension product in the presence of DNA polymerase activity;
    (c) incubating the contacted prepared sample and substrate of (b) under conditions suitable for DNA polymerase activity to generate the extension product from the substrate; and
    (d) amplifying at least a portion of the extension product of (c) to generate an amplicon and detecting the amplicon, thereby indicating the presence of the bacterium or fungus.

2. The method of claim 1, wherein the bacterium or fungus detected is a viable bacterium or fungus in the sample.

3. The method of claim 1, wherein the bacterium or fungus detected is an intact bacterium or fungus in the sample.

4. The method of claim 1, wherein the polymerase substrate is immobilized.

5. The method of claim 1, wherein the sample in which the bacterium or fungus is detected is a normally sterile body fluid.

6. The method of claim 1, wherein the sample in which the bacterium or fungus is detected is prepared from crude cell lysates or purified cell fractions.

7. The method of claim 1, wherein the method further comprises conducting a complete or partial bacterium or fungus genome and or transcriptome sequence analysis.

8. The method of claim 7, wherein the complete or partial bacterium or fungus genome and or transcriptome sequence analysis can be performed simultaneously, in concert, or in parallel using a single sample preparation.

9. The method of claim 7, wherein the complete or partial bacterium or fungus genome and or transcriptome sequence analysis of the bacterium or fungus further comprises a method for the diagnostic measure and detection of agents with anti-microbial and or anti-polymerase activity useful in the management of patients.

10. The method of claim 1, wherein the sample comprises a blood or blood culture sample.

11. The method of claim 10, wherein the bacterium or fungus are recovered from the prepared sample of step (a) and then performing step (b) to (d) with the recovered bacterium or fungus instead of the prepared sample.

12. A method for detecting the presence of a bacterium or fungus in a blood or blood culture sample, wherein DNA polymerase activity is detected as an indicator of the presence of said bacterium or fungus in said sample, which method comprises:
    (a) recovering bacteria or fungi from the blood or blood culture sample;
    (b) contacting the recovered bacteria or fungi with a nucleic acid molecule which acts as a substrate for polymerase activity, wherein the substrate is a partially double-stranded DNA substrate consisting of a sense strand DNA oligonucleotide and an antisense strand DNA oligonucleotide, wherein the two strands overlap to form a double-stranded region and a single-stranded portion of the antisense strand acts as a template with the sense strand of the double-stranded region acting as a primer to create an extension product in the presence of DNA polymerase activity;
    (c) incubating the thus contacted recovered bacteria or fungi of (b) under conditions suitable for DNA polymerase activity to generate the extension product from the substrate; and
    (d) amplifying at least a portion of the extension product of (c) to generate an amplicon and detecting the amplicon, thereby indicating the presence of the bacterium or fungus.

13. The method of claim 12, further comprising performing lysis of the recovered bacteria or fungi prior to performing step (b).

14. The method of claim 11, further comprising performing lysis of the recovered bacteria or fungi prior to performing step (b) to (d) with the lysed recovered bacteria or fungi instead of the prepared sample.

* * * * *